United States Patent [19]

Cerami et al.

[11] Patent Number: 4,758,583
[45] Date of Patent: Jul. 19, 1988

[54] METHOD AND AGENTS FOR INHIBITING PROTEIN AGING

[75] Inventors: Anthony Cerami, Flanders, N.J.; Peter C. Ulrich; Michael Brownlee, both of New York, N.Y.

[73] Assignee: The Rockefeller University, New York, N.Y.

[21] Appl. No.: 798,032

[22] Filed: Nov. 14, 1985

Related U.S. Application Data

[63] Continuation-in-part of Ser. No. 590,820, Mar. 19, 1984, Pat. No. 4,665,192.

[51] Int. Cl.[4] ............... A61U 31/195; A61U 31/415; A61U 37/52; C12N 1/06; C07C 128/00; C07C 129/00
[52] U.S. Cl. .................... 514/399; 435/260; 514/561; 514/631; 564/230
[58] Field of Search ............... 435/260; 514/634, 399, 514/561, 631; 564/230

[56] References Cited

FOREIGN PATENT DOCUMENTS 134099 11/1969 Czechoslovakia.
0111211 11/1982 European Pat. Off..

OTHER PUBLICATIONS

Brownlee et al., *Ann. Int. Med.*, vol. 101, No. 4, pp. 527–537, (1984).
Dabrowski et al., *Acta Physiol. Pol.*, vol. 34, No. I, pp. 91–97, (1983).
Dabrowski et al., *Agents and Actions*, vol. 14, No. 3/4, (1984), pp. 458–460.
Beaven et al., *J. Pharm. Exp. Ther.*, vol. 165, No. 1, pp. 14–22, (1969).
Baylin et al., *Experimentia*, vol. 31, pp. 564–564, (1975).
Brownlee et al., *Science*, vol. 232, pp. 1629–1632, (1986).
Hollis et al., *Diabetologia*, vol. 28, pp. 282–285, (1985).
Monnier et al., *Proc. Natl. Acad. Sci. USA*. vol. 81, pp. 583–587, (1984).
Kohn et al., *Diabetes*, vol. 33, No. 1, Jan. 1984, pp. 57–59.
*Diabetes*, Bol. 35, Supp. 1, p. 42A (1986).
Brownlee et al., *Diabetes*, vol 34, No. 9, Sep. 1985, pp. 938–940.

*Primary Examiner*—Stanley J. Friedman
*Attorney, Agent, or Firm*—David A. Jackson; Richard M. Goldberg; Barbara L. Renda

[57] ABSTRACT

The present invention relates to compositions and methods for inhibiting protein aging. Accordingly, a composition is disclosed which comprises an agent or compound capable of inhibiting the formation of advanced glycosylation end products of target proteins by reacting with the carbonyl moiety of the early glycosylation product of such target proteins formed by their initial glycosylation. Suitable agents may contain an active nitrogen-containing group, such as a hydrazine group, and may further be at least partially derived from amino acids. Particular agents comprise aminoguanidine, α-hydrazinohistidine and lysine. The method comprises contacting the target protein with the composition. Both industrial and therapeutic applications for the invention are envisioned, as food spoilage and animal protein aging can be treated.

6 Claims, 5 Drawing Sheets

Covalent Trapping of BSA by
Nonenzymatically Glycosylated Collagen

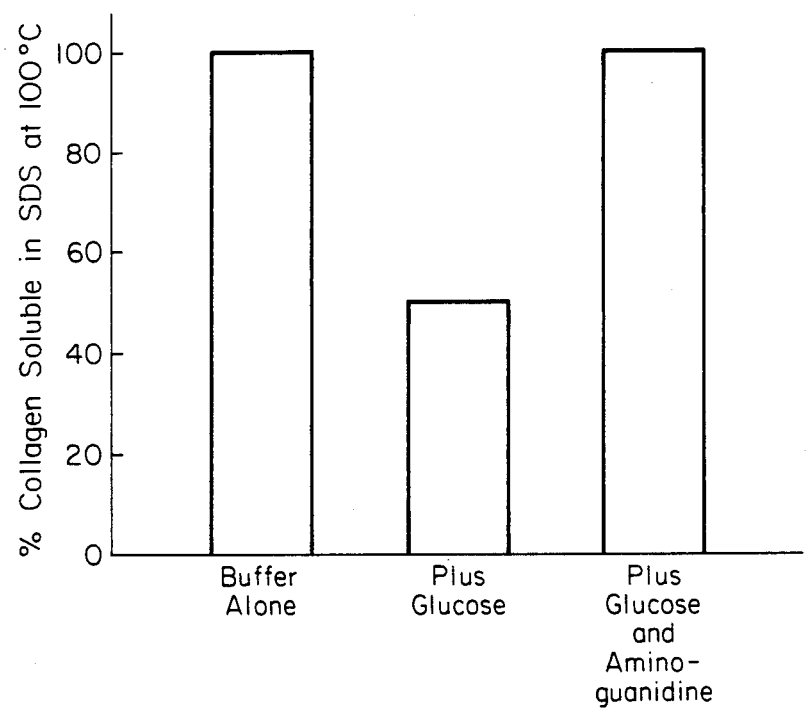

Inhibition of Advanced Glycosylation
Product Formation in vivo

METHOD AND AGENTS FOR INHIBITING PROTEIN AGING

This invention was made with partial assistance from grants from the National Institutes of Health and the Brookdale Foundation.

CROSS REFERENCE TO RELATED APPLICATIONS

The present application is a Continuation-In-Part of copending application Ser. No. 590,820, filed Mar. 19, 1984, by Anthony Cerami, now U.S. Pat. No. 4,665,192.

RELATED PUBLICATIONS

The Applicants are co-authors of the following articles directed to the subject matter of the present invention: "COVALENT ATTACHMENT OF OF SOLUBLE PROTEINS BY NONENZYMATICALLY GLYCOSYLATED COLLAGEN: ROLE IN THE IN SITU FORMATION OF IMMUNE COMPLEXES", Brownlee M., Pongor S., Cerami A., (1983), J. EXP. MED., Vol. 158, pp. 1739-1744; and "AGING OF PROTEINS: ISOLATION AND IDENTIFICATION OF A FLUORESCENT CHROMOPHORE FROM THE REACTION OF POLYPEPTIDES WITH GLUCOSE", Pongor, S., Ulrich, P., Bencsath, A. A., and Cerami, A., PROC. NATL. ACAD. SCI. USA, Vol. 81, pp. 2684-2688, (May, 1984), both of which are incorporated herein by reference.

BACKGROUND OF THE INVENTION

The present invention relates generally to the aging of proteins resulting from reaction of glucose, and particularly to the nonenzymatic glycosylation of proteins and subsequent reactions leading to advanced glycosylation end products, and to methods and agents for their inhibition.

The reaction between glucose and proteins has been known for some time. Its earliest manifestation was in the appearance of brown pigments during the cooking of food, which was identified by Maillard in 1912, who observed that glucose or other reducing sugars react with amino acids to form adducts that undergo a series of dehydrations and rearrangements to form stable brown pigments. Maillard, L. C. (1912) C.R. Acad. Sci., Vol. 54, pp. 66-68.

In the years that followed the initial discovery by Maillard, food chemists studied the hypothesized reaction in detail and determined that stored and heat treated foods undergo nonenzymatic browning as a result of the reaction between glucose and the polypeptide chain, and that the proteins are resultingly cross-linked and correspondingly exhibit decreased bioavailability. Finot, P. A. (1982) in *Modification of Proteins*, eds, Feeney, R. E. and Whitaker, J. R., American Chemical Society, Vol. 198, pp. 91-124, Washington, D.C. At this point, it was determined that the pigments responsible for the development of the brown color that develops as a result of protein glycosylation possessed characteristic spectra and fluorescent properties, however the chemical structure of the pigments had not been specifically elucidated.

The reaction between reducing sugars and food proteins discussed above was found in recent years to have its parallel in vivo. Thus, the nonenzymatic reaction between glucose and the free amino groups on proteins to form a stable amino, 1-deoxy ketosyl adduct, known as the Amadori product, has been shown to occur with hemoglobin, wherein a rearrangement of the amino terminal of the $\beta$-chain of hemoglobin by reaction with glucose, forms the adduct known as hemoglobin $A_{1c}$. The reaction has also been found to occur with a variety of other body proteins, such as lens crystallins, collagen and nerve proteins. See, Bunn, H. F., Haney, D. N., Gabbay, K. H. and Gallop, P. H., (1975) Biochem. Biophys. Res. Comm. Vol. 67, pp. 103-109; Koenig, R. J., Blobstein, S. H. and Cerami, A., (1977) J. Biol. Chem. Vol. 252, pp. 2992-2997; Monnier, V. M. and Cerami, A., (1983) in Maillard Reaction in Food and Nutrition, ed. Waller, G. A., American Chemical Society, Vol. 215, pp. 431-448; and Monnier, V. M. and Cerami, A., (1982) Clinics in Endocrinology and Metabolism Vol. 11, pp. 431-452. Moreover, brown pigments with spectral and fluorescent properties similar to those of late-stage Maillard products have also been observed in vivo in association with several long-lived proteins, such as lens proteins and collagen from aged individuals. An age related linear increase in pigment was observed in human dura collagen between the ages of 20 to 90 years. See, Monnier, V. M. and Cerami, A. (1981) Science, Vol. 211, pp. 491-493; Monnier, V. M. and Cerami, A., (1983) Biochem. Biophys. Acta, Vol. 760, pp. 97-103; and, Monnier, V. M., Kohn, R. R. and Cerami, A., "Accelerated Age-Related Browning of Human Collagen in Diabetes Mellitus", (1984) Proc. Nat. Acad. Sci. Vol. 81, pp. 583-587. Interestingly, the aging of collagen can be mimicked in vitro by the cross-linking induced by glucose; and the capture of other proteins and the formation of adducts by collagen, also noted, is theorized to occur by a crosslinking reaction, and is believed to account for the observed accumulation of albumin and antibodies in kidney basement membrane. See, Brownlee, M., Pongor, S. and Cerami, A., (1983) J. Exp. Med., Vol. 158, pp. 1739-1744; and Kohn, R. R., Cerami, A. and Monnier, V. M., (1984) Diabetes, Vol. 33, No. 1, pp. 57-59.

In parent application Ser. No. 590,820, and in Pongor, S. M., et al., Supra., both incorporated herein by reference, a fluorescent chromophore was isolated and identified which was found to be present in certain browned polypeptides such as bovine serum albumin and poly-L-lysine, and was assigned the structure 2-furoyl-4(5)-2(furanyl)-1H-imidazole. The compound was found to exist in a tautomeric state and has incorporated in its structure two peptide-derived amine nitrogens. The incorporation of these amine nitrogens and two glucose residues in the compound suggested that its peptide-bound precursor may be implicated in the in vivo crosslinking of proteins by glucose, which is observed in the late stage of the Maillard process. [See Chang, J. C. F., Ulrich, P. C., Bucala, R., and Cerami, A. (1985) J. Biol. Chem. Vol. 260, pp. 7970-7974]. This chromophore made possible the identification of the advanced glycosylation end products and assisted additional investigations seeking to clarify the protein aging process and if possible, to identify the specific chemistry involved in an effort to develop methods and agents for its inhibition. It is to this purpose that the present application is directed.

SUMMARY OF THE INVENTION

In accordance with the present invention, a method and associated agents are disclosed for the inhibition of protein aging. In particular, agents for inhibiting protein aging due to the formation of advanced glycosylation end products may be selected from those materials capable of reacting with the early glycosylation product from the reaction of glucose with proteins and preventing further reactions. Thus, for example, compounds or compositions having active nitrogen-containing substituents such as hydrazine groups, have been theorized to be suitable, and compounds such as aminoguanidine, α-hydrazinohistidine and lysine have been found to be suitable. These agents appear to react with the early glycosylation product at its reactive carbonyl and thereby prevent the same from later forming the advanced glycosylation end products which lead to protein crosslinks.

The present invention also relates to a method for inhibiting protein aging by contacting the initially glycosylated protein at the stage of the early glycosylation product with a quantity of one or more of the agents of the present invention. In the instance where the present method has industrial application, one or more of the agents may be applied to the proteins in question, either by introduction into a mixture of the same in the instance of a protein extract, or by application or introduction into foodstuffs containing the protein or proteins, all to prevent premature aging and spoilage of the particular foodstuffs.

In the instance where the present method has therapeutic application, the animal host intended for treatment may have administered to it a quantity of one of more of the agents, in a suitable pharmaceutical form. Administration may be accomplished by known techniques, such as oral, topical and parenteral techniques such as intradermal subcutaneous, intravenous or intraperitoneal injection, as well as by other conventional means. Administration of the agents may take place over an extended period of time at a dosage level of, for example, up to about 25 mg/kg.

The ability to inhibit the formation of advanced glycosylation end products carries with it significant implications in all applications where protein aging is a serious detriment. Thus, in the area of food technology, the retardation of food spoilage would confer an obvious economic and social benefit by making certain foods of marginal stability less perishable and therefore more available for consumers. Spoilage would be reduced as would the expense of inspection, removal and replacement, and the extended availability of the foods could aid in stabilizing their price in the marketplace. Similarly, in other industrial applications where the perishability of proteins is a problems, the admixture of the agents of the present invention in compositions containing such proteins would facilitate the extended useful life of the same. Presently used food preservatives and discoloration preventatives such as sulfur dioxide, known to cause toxicity including allergy and asthma in animals, might be replaced with compounds such as those described herein.

The present method has particular therapeutic application as the Maillard process acutely affects several of the significant protein masses in the body, among them collagen, elastin, lens proteins, and the kidney glomerular basement membranes. These proteins deteriorate both with age (hence the application of the term "protein aging") and as one of the sequelae of diabetes. Consequently, the ability to either retard or substantially inhibit the formation of advanced glycosylation end products carries the promise of favorably treating a significant adverse effect of diabetes and of course, improving the quality and perhaps duration of animal life.

Accordingly, it is a principal object of the present invention to provide a method for inhibiting the extensive cross-linking of proteins that occurs as an ultimate consequence of the reaction of the proteins with glucose, by correspondingly inhibiting the formation of advanced glycosylation end products.

It is a further object of the present invention to provide a method as aforesaid which is characterized by a reaction with an initially glycosylated protein identified as early glycosylation products.

It is a further object of the present invention to provide a method as aforesaid which prevents the rearrangement and cross-linking of the said early glycoslyation products to form the said advanced glycosylation end products.

It is a yet further object of the present invention to provide agents capable of participating in the reaction with the said early glycosylation products in the method as aforesaid.

It is a still further object of the present invention to provide therapeutic methods for treating the adverse consequences of protein aging, manifest in the embrittlement of animal protein and the browning and spoilage of foodstuffs.

Other objects and advantages will become apparent to those skilled in the art from a consideration of the ensuing description which proceeds with reference to the following illustrative drawings.

BRIEF DESCRIPTION OF THE DRAWINGS

FIG. 3A is a graph of the degree of solubilization of collagen incubated with glucose, with and without treatment with an agent of the present invention.

DETAILED DESCRIPTION OF THE PREFERRED EMBODIMENT

Figure 1:
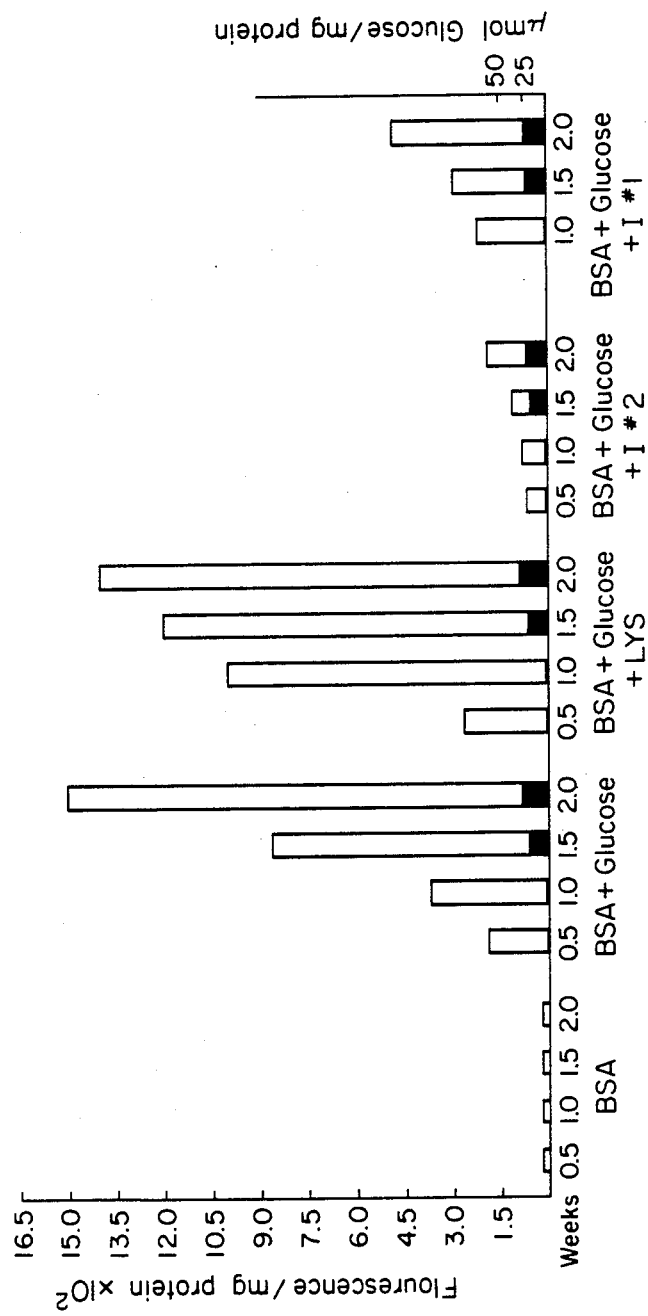
FIG. 1 is a graph showing the results of studies aimed at inhibiting the formation of advanced glycosylation end products in albumin which had been reacted with a quantity of glucose, on an in vitro basis.

In accordance with the present invention, a composition and associated methods have been developed which are believed to inhibit the formation of advanced glycosylation end products in a number of target proteins existing in both animals and plant material. In particular, the invention relates to a composition which may contain one or more agents that are capable of inhibiting the formation of advanced glycosylation end products on such target proteins, by reacting with the carbonyl moiety of the early glycosylation product that is formed by the initial glycosylation of the protein.

It is the carbonyl group located near the junction between the sugar and protein segments of the early glycosylation product that is theorized to comprise an active site that causes the further cross-linking of the protein to form the advanced glycosylation end product, and likewise contributes to the entrapment of other proteins that is evident in the development in vivo of conditions such as skin wrinkling, certain kidney diseases, atherosclerosis, osteoarthritis and the like. Similarly, plant material that undergoes nonenzymatic browning deteriorates and in the case of foodstuffs, becomes spoiled and inedible. Thus, the reaction with this carbonyl moiety is believed to inhibit the late stage Maillard effect.

The rationale of the invention is to use agents which block the post-glycosylation step, i.e., the formation of fluorescent chromophores such as that identified in Pongor, etal., supra. whose presence is associated with, and leads to, the adverse sequelae of diabetes and aging. An ideal agent would prevent the formation of the chromophore and its associated cross-links of proteins to proteins and trapping of proteins on the other proteins, such as occurs in arteries and in the kidney.

The present invention does not attempt to prevent initial protein glycosylation, as it would be nearly impossible to use agents which prevent the reaction of glucose with protein amino groups. The agents that are capable of preventing initial glycosylation are likely to be highly toxic, and since the initial glycosylation comes to equilibrium in about three weeks, there is inadequate time available to achieve this objective. Instead, the ideal agent would prevent or inhibit the long-term, post-glycosylation steps that lead to the formation of the ultimate advanced glycosylation end product which are a direct cause of the pathology associated with aging and diabetes.

Accordingly, the compositions useful in the present invention comprise or contain agents capable of reacting with the active carbonyl intermediate of the early glycosylation product. Suitable agents include compounds having an active nitrogen-containing group or substituent such as a hydrazine group. Also, the agent or compound may be at least partially derived from an amino acid, including the esters and amides thereof, as compounds having this derivation are generally biocompatible with the target proteins to be contacted. For example, the agent may comprise a compound selected from the group consisting of aminoguanidine, α-hydrazinohistidine and lysine, and possibly mixtures of these agents or compounds. Each of these agents or compounds possesses an active nitrogen-containing substituent that is believed to react with the carbonyl of the early glycosylation product. Consequently, reaction of the agents with the glycosyl-lysine moiety of a protein would prevent this moiety from forming crosslinks with other groups.

Hollis and Strickberger (Diabetologia 28:282-5 [1985]) found that in vivo administration of the compound α-hydrazinohydrazine, a known inhibitor of the enzyme histidine decarboxylase, reduces the accumulation of albumin in the aortas of rats. The authors proposed that the drug acted to reduce production of histamine in this tissue, and that histamine is therefore the mediator of low density lipoprotein accumulation which is implicated in atherosclerotic disease. The findings of Hollis and Strickberger are distinguishable from the concept and application of the present invention on several grounds. A primary distinction is that the authors were concerned with protein accumulation that is observed in diabetic animals, and not advanced nonenzymatic glycosylation of proteins. Moreover, the mechanism of histamine synthesis supression by α-hydrazinohistidine suggested by the authors, is functionally distinct from the underlying concept of the present invention, and it is believed, may even be placed in question by the latter.

Thus, the agents of the present invention have been identified and tested on the basis of their ability to react with the carbonyl moiety of the early glycosylation product, and would not have been suggested from the work of Hollis and Strickberger. In particular, aminoguanidine is known to increase levels of histamine (See Lindberg, S., Tornqvist, A., "The Inhibitory Effect of Aminoguanidine on Histamine Catabolism in Human Pregnancy", ACTA OBSTET. GYNECOL. SCAND., 45: 131–139, 1966), and α-Hydrazinohistidine and aminoguanidine therefore have opposing effects on histamine levels. It can therefore be seen that the present findings that both α-hydrazinohistidine and aminoguanidine have efficacy in vivo and in vitro to reduce protein crosslinking rules out from consideration and consequently distinguishes the mechanism proposed by Hollis and Strickberger as the explanation of the manner in which these drugs might work to reduce advanced glycosylation end product formation.

The compound aminoguanidine is known to have low toxicity in animals. According to the 1978 Registry of Toxic Effects of Chemical Substances, aminoguanidine base has a $LD_{50}$ when administered subcutaneously of 1258 mg/kg in rats and 963 mg/kg in mice. The hydrochloride derivative had a $LD_{50}$ in rats of 2984 mg/kg when given subcutaneously. The latter compound exhibits very low toxicity.

In the instance where the composition of the present invention is utilized for in vivo or therapeutic purposes, it may be noted that the compounds or agents used therein are biocompatible. Pharmaceutical compositions may be prepared with a pharmaceutically effective quantity of the agents or compounds of the present invention and may include a pharmaceutically acceptable carrier, selected from known materials utilized for this purpose. Such compositions may be prepared in a variety of forms, depending on the method of administration. For example, aminoguanidine may be derivatized to the hydrochloride salt from the commercially available bicarbonate salt to improve its solubility and to make it less irritating for intraperitoneal injection. Also, a liquid form would be utilized in the instance where administration is by intravenous or intraperitoneal injection, while, if appropriate, tablets, capsules, etc., may be prepared for oral administration. For application to the skin a lotion or ointment may be formulated with the agent in a suitable vehicle, perhaps including a carrier to aid in penetration into the skin. Other suitable forms for administration to other body tissues are contemplated.

The present invention likewise relates to methods for inhibiting the formation of advanced glycosylation end products, which comprise contacting the target proteins with the composition of the present invention. In the instance where the target proteins are contained in foodstuffs, whether plant or animal origin, these foodstuffs could have applied to them by various conventional means a composition containing the present agents. Likewise, in the instance where therapeutic applications are intended, the animals to be treated would have administered to them a regular quantity of the pharmaceutical composition of the present invention. Administration could take place for example daily, and an effective quantity of the agent or compound of the present invention could range up to 25 mg/kg of body weight of the animal. A topical preparation may, for example, include up to 10% of the agent or composition in an ointment or lotion for application to the skin. Naturally, some variation in these amounts is possible, and the suggested amounts are provided in fulfillment of applicants' duty to disclose the best mode for the practice of the present invention.

As is apparent from a discussion of the environment of the present invention, the present methods and compositions hold the promise for arresting the aging of key proteins both in animals and plants, and concomitantly, conferring both economic and medical benefits as a result thereof. In the instance of foodstuffs, the administration of the present composition holds the promise for retarding food spoilage thereby making foodstuffs of increased self life and greater availability to consumers. Replacement of currently-used preservatives, such as sulfur dioxide known to cause allergies and asthma in humans, with non-toxic, biocompatible compounds is a further advantage of the present invention.

The therapeutic implications of the present invention relate to the arrest of the aging process which has as indicated earlier, been identified in the aging of key proteins by advanced glycosylation and cross-linking. Thus, body proteins such as collagen, elastin, lens proteins, nerve proteins and kidney glomerular basement membranes would all benefit in their longevity and operation from the practice of the present invention. It is further theorized that the present invention would reduce the incidence of pathologies involving the entrapment of proteins by cross-linked target proteins, such as atherosclerosis, osteoarthritis, periarticular rigidity, loss of elasticity and wrinkling of skin, stiffening of joints, glomerulonephritis, etc. Likewise, all of these conditions are in evidence in patients afflicted with diabetes mellitus. Thus, the present therapeutic method is relevant to treatment of the noted conditions in patients either of advanced age or those suffering from one of the mentioned pathologies.

The present invention will be better understood from a consideration of the following illustrative examples, reviewing the selection and testing of certain of the agents of the present invention on both an in vitro and in vivo basis.

EXAMPLE I

To measure the ability of certain of the agents of the present invention to inhibit the production of advanced glycosylated end products in vitro, albumin and glucose were incubated together for two weeks in the presence of several test agents. Sample were taken at regular intervals for analysis. Advanced glycosylation endproducts were measured as appearance of fluorescent compounds, and early glycosylation products were measured by incorporation of radiolabeled glucose into albumin. Reaction conditions were as follows. Each mixture contained 6 mg/mL bovine serum albumin, 200 mM glucose, 200 mM test agent (either aminoguanidine hydrochloride, αhydrazinohistidine, or lysine), and approximately $9.5 \times 10^6$ counts per minute of 14C-glucose in 0.5M phosphate buffer, pH 7.6. The radiolabeled glucose was prepurified before use to eliminate breakdown products which might react with the albumin and lead to an erroneous indication of the degree of early glycosylation product formation. Reaction mixtures were incubated at 37° C. and samples were taken after 0.5, 1.0, 1.5, and 2 weeks. Control mixtures lacked glucose or agent.

After the incubation periods, samples were treated as follows. After dialysis to remove all unbound glucose, the amount of protein present was measured with a standard dye-binding assay. The amount of glucose which became bound to the albumin, a measure of early glycosylation products, was determined by precipitating albumin with trichloroacetic acid and measuring the radioactivity of the bound glucose using scintillation counting. Advanced glycosylation endproducts were quantitated by determining the fluorescence of the albuminas described in parent application Ser. No. 590,820, and as described by Pongor et al., supra. Spectral measurements on excitation and emission maxima were made on all samples to ensure that these values had not been shifted as a result of adduct formation with inhibitors.

The results of this experiment are expressed graphically in FIG. 1. For each sample, incorporation of radiolabeled glucose is indicated by the solid portion of the bar, and fluorescence is indicated in the open portion of the bar. All values are expressed as per milligram of albumin. In all further discussions, aminoguanidine refers to the hydrochloride derivative. The results show that glucose and albumin react to form a large amount of fluorescent advanced glycosylation endproducts after 0.5, 1, 1.5, and 2 weeks of incubation ("GLUCOSE+BSA"). Inclusion of 200 mM aminoguanidine dramatically reduced by as much as eight-fold the formation of fluorescent compounds, by comparison with the control samples after a two week incubation ("BSA+GLUCOSE+I#2"). Inclusion of 200 mM α-hydrazinohistidine also reduced formation of advanced glycosylation endproducts as measured by fluorescence ("BSA+GLUCOSE+I#1"). Lysine appeared to cause an increase in fluorescent compound formation ("BSA+GLUCOSE+LYS"), but as will be seen in the next experiment, it had the ability to reduce protein crosslinking. The amount of early glycosylation endproducts, as measured by glucose incorporation, was nearly unchanged in all reactions. The control incubation without glucose showed little development of fluorescent products (A).

These results show that aminoguanidine, and to a lesser extent, α-hydrazinohistidine, reduce the formation of fluorescent compounds when glucose and albumin react over time, and indicate that these two agents reduce the amount of advanced glycosylation endproducts which form. The agents do not alter the formation of early glycosylation products.

EXAMPLE II

To more precisely measure the effect of the agents on the inhibition of protein crosslinking, an assay system was devised to measure the extent of in vitro binding of a soluble protein to an insoluble protein. This assay system mimicks the events which occur in tissues in which serum proteins become bound to proteins in extravascular matrix and which lead to accumulation of protein and narrowing of vessel lumina in several other tissues. These events in vivo give rise to kidney disease and atherosclerotic disease, and lead to the pathologies associated with diabetes and aging.

To measure protein trapping (i.e., binding or accumulation), gelatin (collagen) was coupled to activated agarose beads (Affigel 10, Bio-Rad Laboratories) by routine methods. After coupling, all remaining active sites on the beads were quenched by reaction with glycine ethyl ester.

The beads were incubated for two weeks with bovine serum albumin and 400 mM glucose-6-phosphate, a more reactive form of glucose which forms early glycosylation products with proteins more rapidly than does glucose. Also included in some experiments were the test agents, aminoguanidine, α-hydrazinohistidine, or lysine, at a concentration of 200 mM. The bovine serum albumin was radioiodinated so that the amount which became bound to the beads could be measured. The amount of radiolabel that became bound to the beads in a direct measure of protein trapping.

Figure 2:
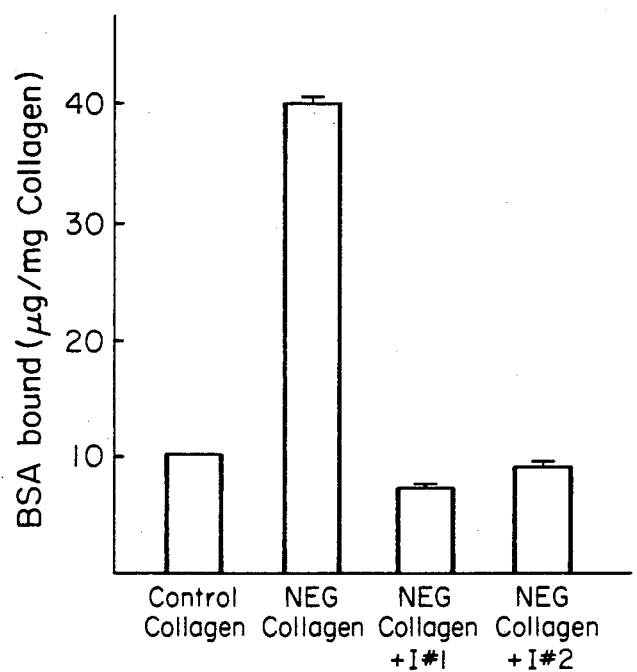
FIG. 2 is a graph showing the results of studies aimed at inhibiting protein entrapment and accumulation by glycosylated structural proteins such as collagen.

After a two-week incubation of the reaction mixtures at 37° C., the beads were washed extensively with chaotropic agents and the covalently bound radioactivity was determined. The results are set forth in FIG. 2.

The left bar shows the control level of radiolabel incorporated into the beads in the absence of glucose-6-phosphate and in the absence of any test agents ("CONTROL COLLAGEN"). The second bar shows the high amount of incorporation in the presence of glucose-6-phosphate ("NEG. COLLAGEN"). This is likened to the presence of high concentrations of glucose in the blood of uncontrolled patients with diabetes and the pathological sequelae which result.

The figure shows that the amount of protein trapping in the presence of either aminoguanidine ("NEG. COLLAGEN+I#2") or α-hydrazinohistidine ("NEG. COLLAGEN+I#1") is greatly reduced. Lysine alse reduced the amount of protein trapping to an extent similar to that of aminoguanidine (not shown). The results show the potential value of these compounds in vivo for reducing the trapping or soluble protein on to membranes and other tissues, and further evidence that these agents may be of value in reducing the pathogenesis of diabetes and aging.

EXAMPLE III

As a further evaluation of the compound aminoguanidine as a model for the prevention of protein trapping, crosslinking and formation of advanced glycosylation endproducts, the following experiment using calf skin collagen was performed. Collagen is a protein in the skin responsible for the suppleness of skin, and crosslinking leads to wrinkling, decreased elasticity, reduced susceptibility to proteolytic degradation, and other changes.

Collagen from samples of calf skin were extracted into acetic acid and then precipitated with 0.6M sodium chloride. These procedures removed from the solution skin collagen that was already permanently crosslinked or denatured. Native collagen fibrils were reformed by dialysis against 0.02M phophate buffer and these were incubated for 3 weeks at 35° C. in the presence of 140 mM glucose and with or without 200 mM aminoguanidine. After incubation, the samples were dialyzed and the degree of crosslinking was determined by two methods. First, the amount of reacted collagen which could be solubilized by treatment in 2% sodium dodecyl sulfate at 100° C. was measured.

As shown in FIG. 3A, collagen incubated with glucose and aminoguanidine was as soluble as collagen incubated in buffer alone. In contrast, collagen incubated in glucose without aminoguanidine was only 50% as soluble. This is further evidence that aminoguanidine may have utility in the prevention of age-related changes in skin and other tissues.

Figure 3B:
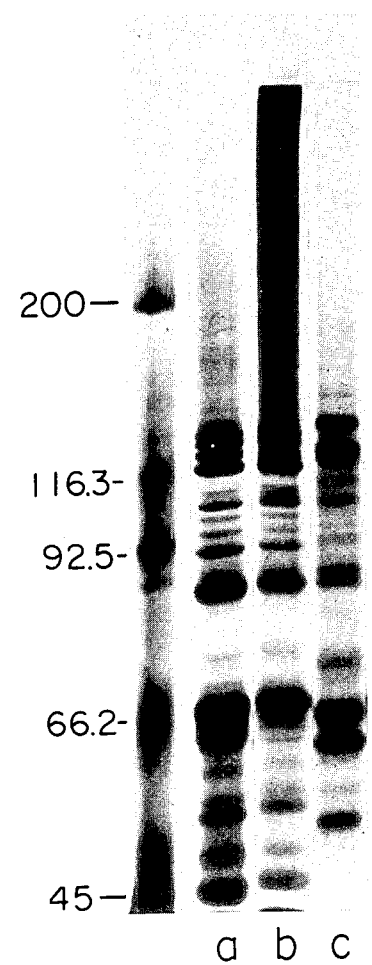
FIG. 3B is a photograph of a polyacrylamide gel showing separation of protein fragments after cyanogen bromide digestion of collagen incubated with glucose with and without an agent of the present invention.

The reacted collagen was further examined by cleaving it into fragments using cyanogen bromide treatment in formic acid. The resulting protein fragments were separated by size by sodium dodecyl sulfate - polyacrylamide gel electrophoresis. After electrophoresis, the protein fragments were identified in the gel using silver staining. The gel is shown in FIG. 3B.

Lane C contains collagen that was incubated with glucose alone. It is noted that a large amount of high molecular weight fragments form a continuous band at the top of the gel, indicating a large range of high molecular weight fragments. Some of this material could not enter the gel and is present in the 30% stacking gel above the gradient gel. Lane B contains the collagen incubated with glucose and aminoguanidine, and it is noted that there is no large amount of high molecular weight material at the top of the lane, as all of the protein fragments separate well in the lower part of the gel. Lanes A and D show collagen incubated in PBS alone or held frozen during the incubation of the other samples, respectively. The far left lane is a series of molecular weight markers. Identical results were observed with and without the presence of disulfide bond reducing agents in the electrophoresis buffer.

The above data indicate that aminoguanidine reduces the amount of crosslinking which occurs when collagen is incubated with glucose, and suggest the utility of this agent for topical application to skin to prevent age-related changes, including loss of elasticity and wrinkling.

The above in vitro experiments all point to the value of aminoguanidine as an agent to inhibit the formation of advanced glycosylation endproducts which form in vitro from proteins incubated in the presence of glucose. As glucose is present in the body and is elevated in amount in diabetes, and as proteins in the body are known to undergo crosslinking and form fluorescent compounds all indicative of advanced glycosylation endproducts, use of this agent in vivo might be useful in the prevention of the pathology associated with diabetes and changes that occur during aging.

Accordingly, the following experiment was performed to test the hypothesis of the present invention in an in vivo environment.

EXAMPLE IV

To measure the level of advanced glycosylation endproducts in vivo, the kidneys of rats were examined for serum proteins which became attached to glomerular basement membranes. This was determined to be a good model in which to study this process as it is known that significant kidney pathology occurs in untreated diabetes as a result of the build-up of extravasated plasma protein in the extravascular matrix in this organ.

The experiment consisted of giving both normal and diabetic rats daily intraperiteoneal doses of the agent aminoguanidine hydrochloride at a dose of 25 mg per kilogram of body weight, for a period of 16 weeks. The hydrochloride salt of aminoguanidine was used as it is more soluble and less irritating than the parent free base compound. Diabetes was induced prior to drug therapy with a single dose of streptozotocin. Control animals, both diabetic and normal, received no drug. At the end of the agent therapy, animals were sacrificed and the kidneys were removed. Each organ was removed from its capsule and the medulla was removed. The remainder of the tissue, principally containing glomeruli, was frozen on dry ice and stored at −70° C. Tissue from 5 animals in each treatment group was combined for processing.

To prepare glomerular basement membranes, tissue was cut into slices and passed through a series of sieves (170, 100 and 270) to separate glomeruli from tubules and other undesired tissue elements as described (Beisswenger, P. J., Spiro, R. G., DIABETES, 22:180-193, 1973.). Glomerular purity was found to be 80-90%. The final material was collected and centrifuged at 1500 rpm for fifteen minutes to pellet the glomeruli, which were frozen at −70° C.

Thawed isolated glomeruli were then disrupted by treatment in a Branson Sonifier 200 cell disrupter for four one-minute intervals on ice with a one-minute rest between sonications. Samples were examined in a phase contrast microscope to ensure that all of the glomeruli were disrupted. Glomerular basement membranes were then pelleted by centrifugation at 3000 rpm for ten minutes, washed with 1M sodium chloride followed by distilled water. The remaining pellet of purified glomerular basement membranes was frozen and lyophilized.

An enzyme immunoassay was used to measure the amount of serum immunoglobulin G (IgG) that became bound to the glomerular basement membranes of the normal and diabetic animals after treatment with and without the agent. To measure IgG, 6 mg samples of lyophilized glomerular basement membrane tissue was suspended in 0.5 mM of 0.05M carbonate buffer, pH 7.6, and 0.5 mM of a 1:5,000 dilution of rat anti-IgG antibody conjugated to alkaline phosphatase (Dynatech Corp.) was added. The mixture was incubated overnight in polystyrene tubes which were preblocked by incubation for two hours in 3% goat serum plus 0.05% Tween 20 in phosphate buffered saline (PBS), followed by two rinses in PBS plus Tween.

After overnight incubation to allow the antibody to bind to any IgG crosslinked to the glomerular basement membranes, the membranes were pelleted by centrifugation at 3200 rpm for five minutes and were washed free of the unbound antibody-enzyme conjugate with four rinses with PBS plus Tween followed by three rinses with distilled water. To measure the amount of antibody-enzyme conjugate remaining bound, 0.5 mM of substrate solution (containing 1 mg/mL para-nitrophenylphosphate in 10% diethanolamine, pH 9.8), was added and incubations were carried out for thirty minutes at room temperature. The reaction was stopped with the addition of 0.2 mL of M sodium hydroxide, and the absorbance at 400 nm was measured.

Figure 4:
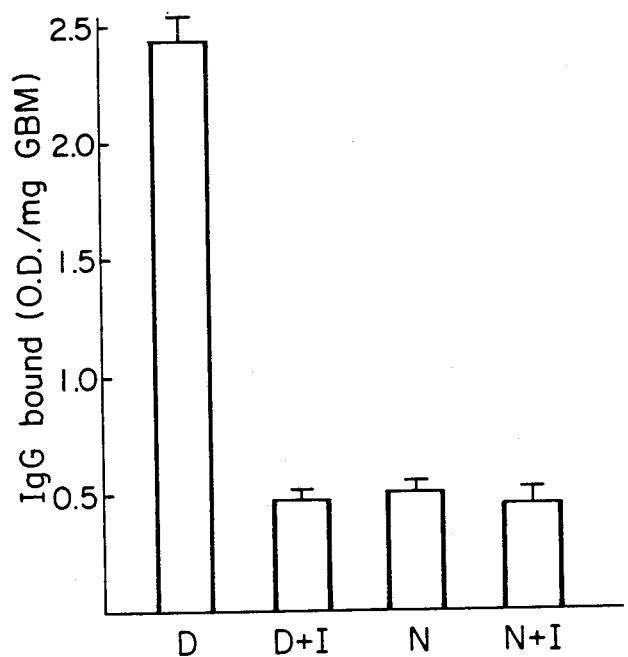
FIG. 4 is a graph of the results of an in vivo study examining the extent of protein bound to the glomerular basement membrane of diabetic rats to certain of which an agent of the present invention had been administered.

FIG. 4 shows the results of this experiment. As can be seen, diabetic animals had a high level of IgG bound to their glomerular basement membranes ("D"), and normal animals had about one-fifth the amount ("N"). Diabetic animals which received daily doses of aminoguanidine hydrochloride showed the same low level of IgG in normal animals ("D+I"). Normal animals receiving the drug had about the same low level ("N+I").

These experiments indicated that aminoguanidine prevented the trapping and accumulation of this plasma protein on the rat glomerular basement membranes. Presumably the trapping of this and other serum proteins in the kidney, eye, on artery walls, and in other tissues known to be affected from this pathology would likewise be reduced. Trapping of lipoproteins on artery walls is known to contribute to atherosclerotic disease.

These in vivo experiments provide further evidence from the in vitro experiments that this type of drug therapy has benefit in reducing the pathology associated with the advanced glycosylation of proteins and the formation of crosslinks between proteins and other macromolecules. Drug therapy may be used to prevent the increased trapping and crosslinking of proteins that occurs in diabetes and aging which leads to sequelae such as arterial disease, including renal disease, hypertension, retinal damage, and extra-vascularly, damage to tendons, ligaments, and other joints. This therapy might retard atherosclerosis and connective tissue changes that occur with diabetes and aging. Both topical, oral, and parenteral routes of administration to provide therapy locally and systemically are contemplated.

This invention may be emobodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

What is claimed is:

1. A method for inhibiting the advanced glycosylation of a target protein comprising contacting the target protein with an amount effective to inhibit the formation of advanced glycosylation end products of a composition comprising an agent capable of reacting with the carbonyl moiety of the early glycosylation product formed by the initial glycosylation of the target protein.

2. The method of claim 1, wherein said agent comprises a compound having an active nitrogen-containing substituent.

3. The method of claim 2, wherein said active nitrogen-containing substituent is a hydrazine group.

4. The method of claim 1, wherein said agent is aminoguanidine, α-hydrazinohistidine, lysine, and mixtures thereof.

5. The method of claim 1, wherein said composition introduced into an isolated quantity of said target protein.

6. The method of claim 1 wherein said target protein is found in foodstuffs and said composition is applied thereto.

* * * * *

UNITED STATES PATENT AND TRADEMARK OFFICE
CERTIFICATE OF CORRECTION

PATENT NO.  : 4,758,583
DATED       : JULY 19, 1988
INVENTOR(S) : ANTHONY CERAMI ET AL.

It is certified that error appears in the above-identified patent and that said Letters Patent is hereby corrected as shown below:

At Column 10, line 8, change "Lane C" to -- Lane B --;
line 14, change "B" to -- C --;
line 19, change "Lanes A and B show" to
-- Lane A shows --;
lines 20-21, please delete "or held frozen during
the incubation of the other samples, respectively".

Signed and Sealed this

Twenty-fifth Day of January, 1994

Attest:

BRUCE LEHMAN

Attesting Officer                Commissioner of Patents and Trademarks